United States Patent
Dyballa et al.

(10) Patent No.: US 9,670,585 B2
(45) Date of Patent: Jun. 6, 2017

(54) ELECTROCHEMICAL COUPLING OF A PHENOL TO A NAPHTHOL

(71) Applicants: Katrin Marie Dyballa, Recklinghausen (DE); Robert Franke, Marl (DE); Dirk Fridag, Haltern am See (DE); Siegfried R. Waldvogel, Gau-Algesheim (DE); Bernd Elsler, Bonn (DE)

(72) Inventors: Katrin Marie Dyballa, Recklinghausen (DE); Robert Franke, Marl (DE); Dirk Fridag, Haltern am See (DE); Siegfried R. Waldvogel, Gau-Algesheim (DE); Bernd Elsler, Bonn (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/773,228

(22) PCT Filed: Dec. 10, 2013

(86) PCT No.: PCT/EP2013/076086
§ 371 (c)(1),
(2) Date: Sep. 4, 2015

(87) PCT Pub. No.: WO2014/135237
PCT Pub. Date: Sep. 12, 2014

(65) Prior Publication Data
US 2016/0017505 A1    Jan. 21, 2016

(30) Foreign Application Priority Data
Mar. 7, 2013 (DE) .................. 10 2013 203 866

(51) Int. Cl.
| | | |
|---|---|---|
| C07C 43/23 | (2006.01) | |
| C25B 3/10 | (2006.01) | |
| C25B 15/08 | (2006.01) | |
| C25B 15/02 | (2006.01) | |
| C25B 9/08 | (2006.01) | |

(52) U.S. Cl.
CPC .............. *C25B 3/10* (2013.01); *C07C 43/23* (2013.01); *C25B 9/08* (2013.01); *C25B 15/02* (2013.01); *C25B 15/08* (2013.01)

(58) Field of Classification Search
None
See application file for complete search history.

(56) References Cited

U.S. PATENT DOCUMENTS

2012/0080320 A1    4/2012  Fischer et al.

FOREIGN PATENT DOCUMENTS

| JP | 2012-528938 | 11/2012 |
|---|---|---|
| WO | WO 2010/139685 A1 | 12/2010 |
| WO | WO 2014/135236 A1 | 9/2014 |
| WO | WO 2014/135371 A1 | 9/2014 |
| WO | WO 2014/135405 A1 | 9/2014 |

OTHER PUBLICATIONS

Kirste et al. (Efficient Anodic and Direct Phenol-Arene C,C Cross-Coupling: The Benign Role of Water or Methanol, Journal of the American Chemical Society, Jan. 2012, vol. 134, pp. 3571-3576).*
Sartori et al.: "Selective Synthesis of unsymmetrical 2,2'-dihydroxylated biaryls via electrophilic arylation of metal phenolates with p-benzoquinone monoketals", Journal of the Chemical Society, Perkin Transactions 1, No. 17, 1995, 5 pages.
Kumar et al.: "Reversal of Polarity in Masked o-Benzoquinones: Rapid Access to Unsymmetrical Oxygenated Biaryls". Organic Letters, vol. 15, No. 14, Jul. 2, 2013, pp. 3546-3549.
Kirste A et al.: "Anodic Phenol-Arene Cross-Coupling Reaction on Boron-Doped Diamond Electrodes". Angewandte Chemie. International Edition, vol. 49, No. 5, Jan. 25, 2010, pp. 971-975.
International Search Report filed on Apr. 11, 2014 for PCT/EP2013/076086 filed on Dec. 10, 2013.
U.S. Appl. No. 14/772,874, filed Sep. 4, 2015, Dyballa, et al.
U.S. Appl. No. 14/773,224, filed Sep. 4, 2015, Dyballa, et al.
U.S. Appl. No. 14/773,102, filed Sep. 4, 2015, Dyballa, et al.
G. Sartori, et al., "Selective synthesis of unsymmetrical 2,2'-dihydroxylated biaryls via electrophilic arylation of metal phenolates with p-benzoquinone monoketals", J. Chem. Soc. Perkin Trans. 1, 1995, (17), pp. 2177-2181.
Resulsts of Kipo Examination in corresponding Korean Patent Application No. 10-2015-7027235, dated Apr. 3, 2017.
G. Sartori, et al., "Selective synthesis of unsymmetrical 2,2'-dihydroxylated biaryls via electrophile arylation of metal phenolates with p-benzoquinone monoketals", J. Chem. Soc. Perkin Trans 1, No. 17, 1995, pp. 2177-2181.
A. Kirste, et al., "Anodic Phenol-Arene Cross-Coupling Reaction on Boron-Doped Diamond Electrodes", vol. 49, 2010, pp. 971-975.

* cited by examiner

*Primary Examiner* — Rosalynd Keys
(74) *Attorney, Agent, or Firm* — Oblon, McClelland, Maier & Neustadt, L.L.P.

(57) ABSTRACT

The invention relates to an electrochemical method for the selective coupling of a phenol to a naphthol which differ in their oxidation potential. The invention also relates to compounds which can be produced by electrochemical coupling.

7 Claims, 3 Drawing Sheets

ELECTROCHEMICAL COUPLING OF A PHENOL TO A NAPHTHOL

Figure 1:
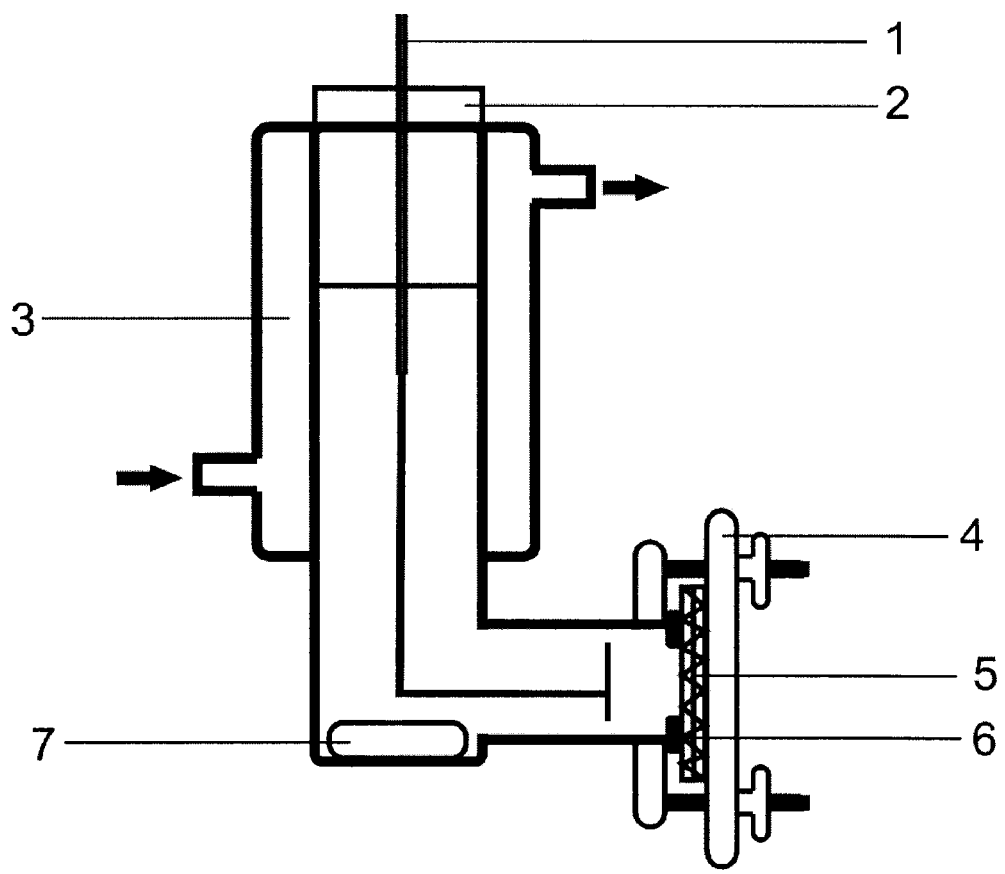

The invention which follows relates to an electrochemical process for coupling a phenol to a naphthol, these having different oxidation potentials. The invention further relates to compounds which can be prepared, for example, by electrochemical coupling.

The terms "phenols" and "naphthols" are used as generic terms in this application and hence also encompass substituted phenols and substituted naphthols.

To date, only an electrochemical coupling of phenol to a naphthol not having any OH group has been described: Kirste et al. Angew. Chem. 2010, 122, 983-987 and Kirste et al. J. Am. Chem. Soc. 2012, 134, 3571-3576.

A problem which occurs in the electrochemical coupling of different molecules is that they have different oxidation potentials $E_{Ox}$. The result of this is that the molecule having the higher oxidation potential has a lower propensity to release an electron (e⁻) to the anode and an H⁺ ion to the solvent, for example, than the molecule having the lower oxidation potential. The oxidation potential $E_{Ox}$ can be calculated via the Nernst equation:

$$E_{Ox} = E° + (0.059/n)*\lg([Ox]/[Red])$$

$E_{Ox}$: electrode potential for the oxidation reaction (=oxidation potential)
$E°$: standard electrode potential
n: number of electrons transferred
[Ox]: concentration of the oxidized form
[Red]: concentration of the reduced form The problem addressed by the invention which follows was that of providing an electrochemical process in which a phenol is coupled to a naphthol, these two molecules having different oxidation potentials In addition, novel compounds were to be synthesized.

Compound of one of the general formulae (I) to (III):

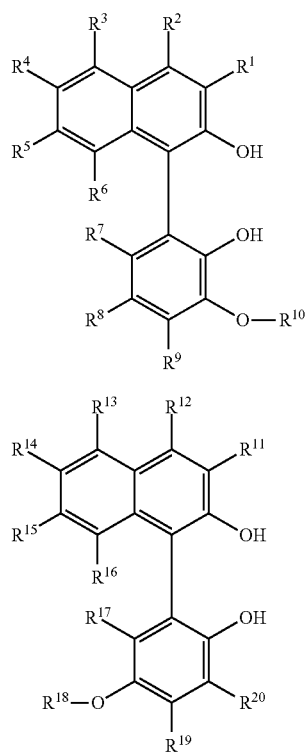

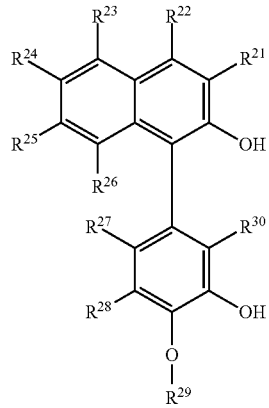

where $R^1$, $R^2$, $R^3$, $R^4$, $R^5$, $R^6$, $R^7$, $R^8$, $R^9$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$, $R^{26}$, $R^{27}$, $R^{28}$, $R^{30}$ are selected from: —H, -alkyl, —O-alkyl, —O-aryl, —S-alkyl, —S-aryl and where $R^{10}$, $R^{18}$, $R^{29}$ are -alkyl.

Alkyl is an unbranched or branched aliphatic carbon chain having 1 to 10 carbon atoms. The carbon chain preferably has 1 to 6 carbon atoms, more preferably 1 to 4 carbon atoms.

Aryl represents aromatic (hydrocarbyl) radicals, preferably having up to 14 carbon atoms, e.g. phenyl- ($C_6H_5$—), naphthyl- ($C_{10}H_7$—), anthryl- ($C_{14}H_9$—), preferably phenyl.

In one embodiment, $R^1$, $R^2$, $R^3$, $R^4$, $R^5$, $R^6$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$, $R^{26}$, $R^{27}$, $R^{28}$, $R^{30}$ are selected from: —H, -alkyl, —O-alkyl, O-aryl.

In one embodiment, $R^1$, $R^2$, $R^3$, $R^4$, $R^5$, $R^6$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$, $R^{26}$, $R^{27}$, $R^{28}$, $R^{30}$ are selected from: —H, -alkyl.

In one embodiment, $R^8$ and $R^{27}$ are -alkyl.

In one embodiment, $R^{20}$ is -alkyl.

In one embodiment, $R^1$, $R^2$, $R^3$, $R^4$, $R^5$, $R^6$, $R^7$, $R^8$, $R^9$, $R^{11}$, $R^{12}$, $R^{13}$, $R^{14}$, $R^{15}$, $R^{16}$, $R^{21}$, $R^{22}$, $R^{23}$, $R^{24}$, $R^{25}$, $R^{26}$ are —H.

In one embodiment, $R^7$, $R^9$, $R^{17}$, $R^{19}$, $R^{28}$, $R^{30}$ are —H.

As well as the compounds, also claimed is a process by which, for example, the abovementioned compounds can be prepared.

Electrochemical process comprising the process steps of:
a) introducing a solvent or solvent mixture and a conductive salt into a reaction vessel,
b) adding a phenol having an oxidation potential $|E_{Ox}1|$ to the reaction vessel,
c) adding a naphthol having an oxidation potential $|E_{Ox}2|$ to the reaction vessel, the substance having the higher oxidation potential being added in excess,
and where: $|E_{Ox}1|-|E_{Ox}2|=|\Delta E|$
and the solvent or solvent mixture is selected such that $|\Delta E|$ is in the range from 10 to 450 mV,
d) introducing two electrodes into the reaction solution,
e) applying a voltage to the electrodes,
f) coupling the phenol to the naphthol to give a cross-coupled product.

Process steps a) to d) can be effected here in any sequence.

The process can be conducted on different carbon electrodes (glassy carbon, boron-doped diamond, graphites, carbon fibres, nanotubes, inter alia), metal oxide electrodes and metal electrodes. In this process, current densities in the range of 1-50 mA/cm² are applied.

The process according to the invention solves the problem stated at the outset.

One aspect of the invention is that the yield of the reaction can be controlled via the difference in the oxidation potentials (|ΔE|) of the two compounds.

For efficient conduct of the reaction, two reaction conditions are necessary:
the compound having the higher oxidation potential has to be added in excess, and
the difference in the two oxidation potentials (|ΔE|) has to be within a particular range.

If the first condition is not met, the main product formed is a compound which arises through the coupling of two molecules having the lower oxidation potential.

If |ΔE| is too small, too much of the compound which arises through the coupling of two molecules having the higher oxidation potential is by-produced, since the latter is added in excess.

If, in contrast, |ΔE| is too large, an excessively high excess of the compound having the higher oxidation potential would be required, which would make the reaction uneconomic.

For the process according to the invention, knowledge of the absolute oxidation potentials of the two compounds is not absolutely necessary. It is sufficient when the difference in the two oxidation potentials relative to one another is known.

A further aspect of the invention is that the difference in the two oxidation potentials (|ΔE|) can be influenced via the solvents or solvent mixtures used.

For instance, the difference in the two oxidation potentials (|ΔE|) can be moved into the desired range by suitable selection of the solvent/solvent mixture.

Proceeding from 1,1,1,3,3,3-hexafluoroisopropanol (HFIP) as the base solvent, a |ΔE| which is too small can be increased, for example, by addition of alcohol. A |ΔE| which is too large can be lowered, in contrast, by addition of water.

The reaction sequence which proceeds is shown in the following scheme:

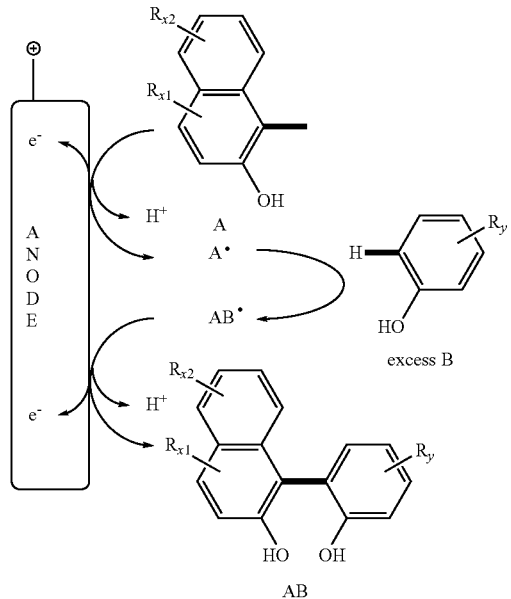

First of all, the compound A having the lower oxidation potential releases an electron to the anode. Because of the positive charge, compound A becomes a very strong acid and spontaneously releases a proton. The radical thus formed then reacts with the compound B which is present in the solution in excess relative to the compound A. The AB radical formed by the coupling releases an electron to the anode and a proton to the solvent.

If the compound having the higher oxidation potential had not been added in excess, the A radical would react with a second compound A to give the corresponding AA compound.

With the aid of the process according to the invention, it has been possible for the first time to couple phenols with naphthols electrochemically in good yields.

In one variant of the process, the substance having the higher oxidation potential is used at least in twice the amount relative to the substance having the lower oxidation potential.

In one variant of the process, the solvent or solvent mixture is selected such that |ΔE| is in the range from 20 mV to 400 mV, preferably in the range from 30 mV to 350 mV.

In one variant of the process, the conductive salt is selected from the group of alkali metal, alkaline earth metal, tetra($C_1$-$C_6$-alkyl)ammonium, 1,3-di($C_1$-$C_6$-alkyl)imidazolium and tetra($C_1$-$C_6$-alkyl)phosphonium salts.

In one variant of the process, the counterions of the conductive salts are selected from the group of sulphate, hydrogensulphate, alkylsulphates, arylsulphates, alkylsulphonates, arylsulphonates, halides, phosphates, carbonates, alkylphosphates, alkylcarbonates, nitrate, tetrafluoroborate, hexafluorophosphate, hexafluorosilicate, fluoride and perchlorate.

In one variant of the process, the conductive salt is selected from tetra($C_1$-$C_6$-alkyl)ammonium salts, and the counterion is selected from sulphate, alkylsulphate, arylsulphate.

In one variant of the process, the phenol has at least one —O-alkyl group.

In one variant of the process, the reaction solution is free of transition metals.

In one variant of the process, the reaction solution is free of substrates having leaving functionalities other than hydrogen atoms.

In one variant of the process, the reaction solution is free of organic oxidizing agents.

In one variant of the process, the phenol is selected from: Ia, IIa, IIIa:

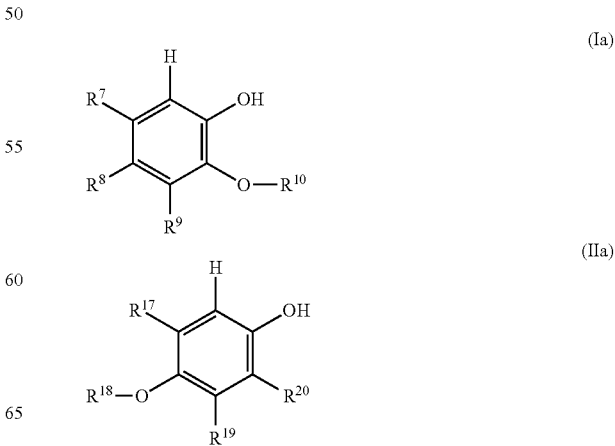

-continued

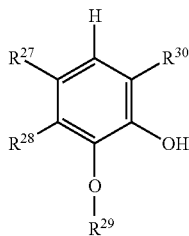
(IIIa)

and the naphthol is selected from: Ib, IIb, IIIb:

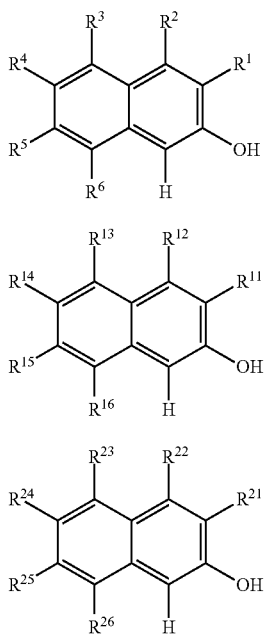

where $R^1, R^2, R^3, R^4, R^5, R^6, R^7, R^8, R^9, R^{11}, R^{12}, R^{13}, R^{14}, R^{15}, R^{16}, R^{17}, R^{19}, R^{20}, R^{21}, R^{22}, R^{23}, R^{24}, R^{25}, R^{26}, R^{27}, R^{28}, R^{30}$ are selected from: —H, -alkyl, —O-alkyl, O-aryl, —S-alkyl, —S-aryl- and
where $R^{10}, R^{18}, R^{29}$ are -alkyl,
and the following combinations are possible here:

| phenol | Ia | IIa | IIIa |
| naphthol | Ib | IIb | IIIb |

The invention is illustrated in detail hereinafter by working examples and a figure.

FIG. 1 shows a reaction apparatus in which the above-described coupling reaction can be performed. The apparatus comprises a nickel cathode (1) and an anode composed of boron-doped diamond (BDD) on silicon (5). The apparatus can be cooled with the aid of the cooling jacket (3). The arrows here indicate the flow direction of the cooling water. The reaction space is closed by a Teflon stopper (2). The reaction mixture is mixed by a magnetic stirrer bar (7). On the anode side, the apparatus is closed by screw clamps (4) and seals (6).

Figure 2:
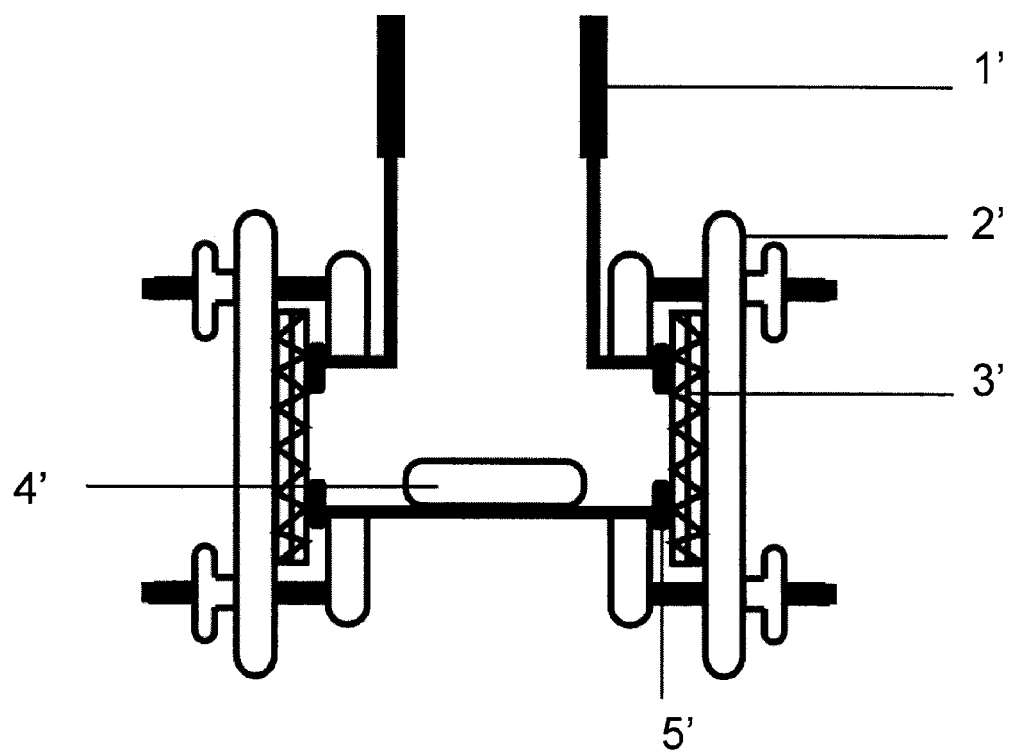

FIG. 2 shows a reaction apparatus in which the above-described coupling reaction can be performed on a larger scale. The apparatus comprises two glass flanges (5'), which are used to apply pressure, through screw clamps (2') and seals, to electrodes (3') composed of carrier materials coated with boron-doped diamond (BDD), or other electrode materials known to those skilled in the art. The reaction space may be provided with a reflux condenser via a glass sleeve (1'). The reaction mixture is mixed with the aid of a magnetic stirrer bar (4').

Figure 3:
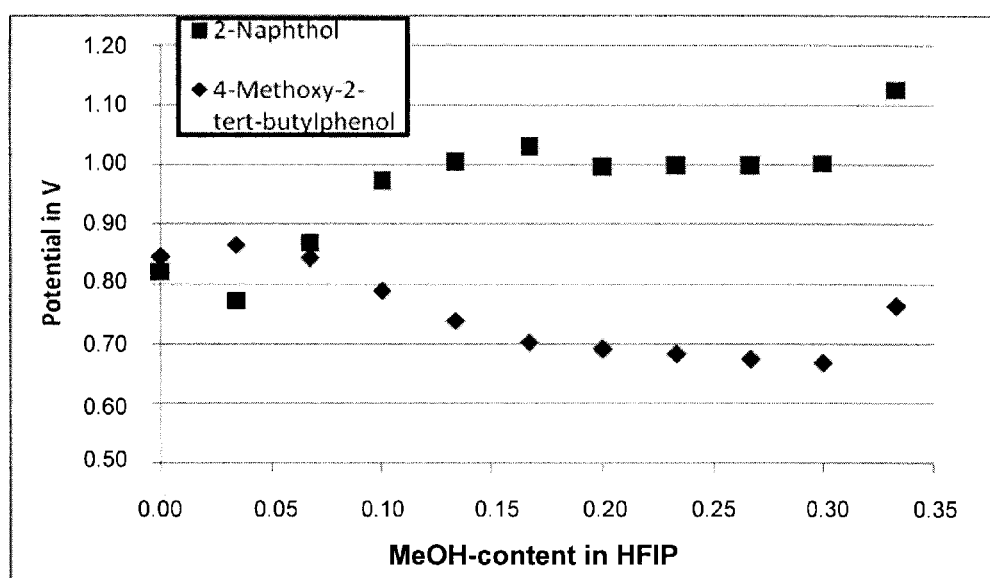

FIG. 3 shows a plot of the respective oxidation potentials with addition of MeOH (successful example of cross-coupling).

ANALYSIS

Chromatography

The preparative liquid chromatography separations via "flash chromatography" were conducted with a maximum pressure of 1.6 bar on 60 M silica gel (0.040-0.063 mm) from Macherey-Nagel GmbH & Co, Düren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) were purified beforehand by distillation on a rotary evaporator.

For thin-layer chromatography (TLC), ready-to-use PSC plates, silica gel 60 F254 from Merck KGaA, Darmstadt, were used. The Rf values are reported according to the eluent mixture used. The TLC plates were stained using a cerium-molybdatophosphoric acid solution as a dipping reagent: 5.6 g of molybdatophosphoric acid, 2.2 g of cerium (IV) sulphate tetrahydrate and 13.3 g of concentrated sulphuric acid in 200 ml of water.

Gas Chromatography (GC/GCMS)

The gas chromatography analyses (GC) of product mixtures and pure substances were effected with the aid of the GC-2010 gas chromatograph from Shimadzu, Japan. Measurement is effected on an HP-5 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme: "hard" method: start temperature 50° C. for 1 min, heating rate: 15° C./min, final temperature 290° C. for 8 min). Gas chromatography mass spectra (GCMS) of product mixtures and pure substances were recorded with the aid of the GC-2010 gas chromatograph combined with the GCMS-QP2010 mass detector from Shimadzu, Japan. Measurement is effected on an HP-1 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme: "hard" method: start temperature 50° C. for 1 min, heating rate: 15° C./min, final temperature 290° C. for 8 min; GCMS: ion source temperature: 200° C.).

Melting Points

Melting points were measured with the aid of the SG 2000 melting point measuring instrument from HWS, Mainz and are uncorrected.

Elemental Analysis

The elemental analyses were conducted in the Analytical Division of the Department of Organic Chemistry at the Johannes Gutenberg University of Mainz on a Vario EL Cube from Foss-Heraeus, Hanau.

Mass Spectrometry

All electrospray ionization analyses (ESI+) were conducted on a QTof Ultima 3 from Waters Micromasses, Milford, Mass. EI mass spectra and the high-resolution EI spectra were measured on an instrument of the MAT 95 XL sector-field instrument type from ThermoFinnigan, Bremen.

NMR Spectroscopy

The NMR spectroscopy studies were conducted on multinuclear resonance spectrometers of the AC 300 or AV II 400 type from Bruker, Analytische Messtechnik, Karlsruhe. The solvent used was $CDCl_3$. The $^1H$ and $^{13}C$ spectra were calibrated according to the residual content of undeuterated solvent according to the NMR Solvent Data Chart from Cambridge Isotopes Laboratories, USA. Some of the $^1H$ and $^{13}C$ signals were assigned with the aid of H,H COSY, H,H NOESY, H,C HSQC and H,C HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported with the number of bonds covered in Hertz (Hz). The numbers reported in the signal assignment correspond to the numbering given in the formula schemes, which need not correspond to IUPAC nomenclature.

General Procedure

The coupling reaction was conducted in an apparatus as shown in FIG. 1.

5 mmol of the compound having the higher oxidation potential are dissolved together with 15 mmol of the compound having the lower oxidation potential in the amounts specified in Table 1 below in 1,1,1,3,3,3-hexafluoroisopropanol (HFIP) and MeOH or in formic acid and MeOH. The electrolysis is effected under galvanostatic conditions. The outer jacket of the electrolysis cell is kept at a temperature of about 10° C. by means of a thermostat, while the reaction mixture is stirred and heated to 50° C. with the aid of a sand bath. After the end of the electrolysis, the cell contents are transferred with toluene into a 50 ml round-bottom flask and the solvent is removed under reduced pressure on a rotary evaporator at 50° C., 200-70 mbar. Unconverted reactant is recovered by means of short-path distillation (100° C., $10^{-3}$ mbar).

| Electrode material | |
| --- | --- |
| Anode: | BDD on Si |
| Cathode: | Ni mesh |
| Electrolysis conditions: | |
| Temperature [T]: | 50° C. |
| Current [I]: | 15 mA |
| Current density [j]: | 2.8 mA/cm$^2$ |
| Quantity of charge [Q]: | 2 F/mol of deficiency component |
| Terminal voltage [$U_{max}$]: | 3-5 V |

Syntheses 1-(2-Hydroxy-3-methoxy-5-methylphenyl)-2-naphthol and 1-(5-hydroxy-4-methoxy-2-methylphenyl)-2-naphthol The electrolysis was performed according to GP1 in an undivided flange cell with a BDD anode. For this purpose, 0.78 g (5 mmol, 1.0 equiv.) of 2-naphthol and 2.18 g (15 mmol, 3.0 equiv.) of 4-methylguaiacol were dissolved in 27 ml of HFIP and 6 ml of MeOH, 0.68 g of MTES were added and the electrolyte was transferred into the electrolysis cell. The solvent and unconverted amounts of reactant are removed under reduced pressure after the electrolysis, the crude product is purified by flash chromatography on silica gel 60 in a 4:1 eluent (CH:EA) and a product mixture was obtained. A second flash chromatography in dichloromethane enables a separation of the two components as a pale red crystalline main product and a colourless crystalline by-product.

1-(2-Hydroxy-3-methoxy-5-methylphenyl)-2-naphthol (Main Product)

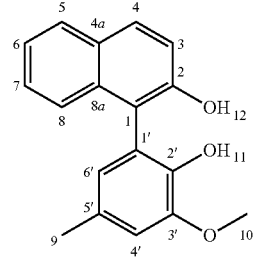 [SMILES: COc1cc(C)cc(-c2c(O)ccc3ccccc23)c1O]

Yield: 899 mg (61%, 3.2 mmol)
GC (hard method, HP-5): $t_R$=15.77 min
$R_f$(CH:EA=4:1)=0.36, $R_f$(DCM)=0.36
$m_p$=145.5° C. (recrystallized from DCM/CH)
$^1H$ NMR (400 MHz, $CDCl_3$) δ=2.39 (s, 3H, 9-H), 3.96 (s, 3H, 10-H), 5.47-5.52 (m, 1H, 12-H), 5.65-5.69 (m, 1H, 11-H), 6.75 (d, 1H, 6'-H), 6.85 (d, 1H, 4'-H), 7.32 (dd, 1H, 3-H), 7.34-7.43 (m, 2H, 6-H/7-H), 7.51 (d, 1H, 8-H), 7.83 (s, 1H, 5-H), 7.85 (d, 1H, 4-H);
Couplings: $^3J_{3\text{-}H, 4\text{-}H}$=9.0 Hz, $^3J_{7\text{-}H, 8\text{-}H}$=8.3 Hz, $^4J_{4'\text{-}H, 6'\text{-}H}$=1.8 Hz;
$^{13}C$ NMR (101 MHz, $CDCl_3$) δ=21.22 (C-9), 56.08 (C-10), 112.06 (C-4'), 116.62 (C-1), 117.81 (C-3), 119.33 (C-1'), 123.36 (C-6/C-7), 124.42 (C-6'), 124.86 (C-8), 126.48 (C-6/C-7), 128.15 (C-4), 129.18 (C-4a), 129.83 (C-5), 130.36 (C-5'), 133.16 (C-8a), 141.72 (C-2'), 147.24 (C-3'), 150.84 (C-2).
HRMS for $C_{18}H_{16}O_3$ (ESI+) [M+Na$^+$]: calc.: 303.0997. found: 303.1003.
MS (EI, GCMS): m/z (%): 280 (100) [M]$^+$, 265 (12) [M-CH$_3$]$^+$, 249 (12) [M-OCH$_3$]$^+$.
Elemental analysis for $C_{18}H_{16}O_3$ calc.: C, 77.12%; H, 5.75%. found: C, 76.96%; H, 5.82%.

1-(5-Hydroxy-4-methoxy-2-methylphenyl)-2-naphthol (By-Product)

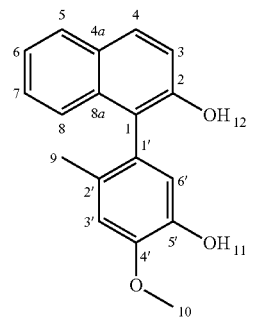 [SMILES: COc1cc(C)c(-c2c(O)ccc3ccccc23)cc1O]

Yield: 106 mg (7%, 0.4 mmol)
GC (hard method, HP-5): $t_R$=15.42 min
$R_f$(CH:EA=4:1)=0.36, $R_f$(DCM)=0.32
$m_p$=182° C. (recrystallized from DCM/CH)
$^1$H NMR (400 MHz, DMSO) δ=1.82 (s, 3H, H-9), 3.82 (s, 3H, H-10), 6.52 (s, 1H, H-6'), 6.89 (s, 1H, H-3'), 7.14 (dd, 1H, H-8), 7.31-7.18 (m, 3H, H-3/H-6/H-7), 7.75 (d, 1H, H-5), 7.78 (d, 1H, H-4), 8.78 (s, 1H, H-11), 9.31 (s, 1H, H-12);
Couplings: $^3J_{3\text{-}H,\ 4\text{-}H}$=7.1 Hz, $^3J_{5\text{-}H,\ 6H}$=8.7 Hz, $^3J_{7\text{-}H,\ 8\text{-}H}$=8.1 Hz, $^4J_{6\text{-}H,\ 8\text{-}H}$=1.5 Hz;
$^{13}$C NMR (101 MHz, DMSO) δ=19.40 (C-9), 56.06 (C-10), 114.31 (C-3'), 118.51 (C-6'), 118.78 (C-3), 120.82 (C-1), 122.78 (C-6), 124.52 (C-8), 126.45 (C-7), 127.84 (C-1'), 128.29, 128.36, 128.70 (C-5/5a/8a), 134.11 (C-2'), 144.52 (C-5'), 147.06 (C-4'), 152.19 (C-2).
HRMS for $C_{18}H_{16}O_3$ (ESI+) [M+Na]$^+$: calc.: 303.0997. found: 303.1004.
MS (EI, GCMS): m/z (%): 280 (100) [M]$^+$, 265 (16) [M-CH$_3$]$^+$, 249 (12) [M-OCH$_3$]+.
Elemental analysis for $C_{18}H_{16}O_3$ calc.: C, 77.12%; H, 5.75%. found: C, 77.19%; H, 5.81%.

1-(3-(Dimethylethyl)-2-hydroxy-5-methoxyphenyl)-2-naphthol

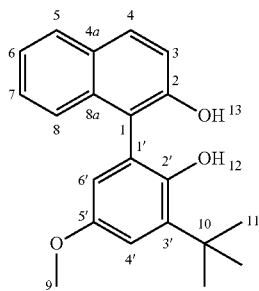

The electrolysis was performed according to GP1 in an undivided flange cell with a BDD anode. For this purpose, 0.72 g (5 mmol, 1.0 equiv.) of 2-naphthol and 2.77 g (15 mmol, 3.0 equiv.) of 2-(dimethylethyl)-4-methoxyphenol are dissolved in 27 ml HFIP and 6 ml MeOH, 0.68 g of MTES are added and the electrolyte is transferred to the electrolysis cell. The solvent and unconverted amounts of reactant are removed under reduced pressure after the electrolysis, the crude product is purified by flash chromatography on silica gel 60 in a 9:1 eluent (CH:EA) and the product is obtained as a colourless solid.

Yield: 1.05 g (63%, 3.2 mmol)
GC (hard method, HP-5): $t_R$=15.75 min
$R_f$(CH:EA=4:1)=0.43
$m_p$=139.9° C. (recrystallized from DCM/CH)
$^1$H NMR (400 MHz, CDCl$_3$) δ=1.46 (s, 9H, 11-H), 3.77 (s, 3H, 9-H), 4.72 (s, 1H, 2'-H), 5.36 (s, 1H, 2-H), 6.63 (d, 1H, 6'-H), 7.08 (d, 1H, 4'-H), 7.32 (d 1H, 3-H), 7.50-7.35 (m, 3H, 6-H/7-H/8-H), 7.87-7.83 (m, 1H, 5-H), 7.89 (d, 1H, 4-H);
$^{13}$C NMR (101 MHz, CDCl$_3$) δ=29.41 (C-11), 35.19 (C-10), 55.68 (C-9), 111.95 (C-6'), 114.18 (C-1), 115.87 (C-4'), 117.63 (C-3), 119.16 (C-1'), 123.89, 124.15 (C-6/C-8), 127.38 (C-7), 128.31 (C-5), 129.19 (C-4a), 130.97 (C-4), 132.99 (C-8a), 139.05 (C-3'), 146.93 (C-2'), 151.94 (C-2), 153.41 (C-5').

HRMS for $C_{21}H_{22}O_3$ (ESI+) [M+Na]$^+$: calc.: 345.1467. found: 345.1465.
MS (EI, GCMS): m/z (%): 322 (100) [M]$^+$, 307 (38) [M-CH$_3$]$^+$.
Elemental analysis for $C_{21}H_{22}O_3$ calc.: 78.23%; H, 6.88%. found: C, 78.18%; H, 6.82%.

Results

Table 1 lists the yields and selectivities:

TABLE 1

| Product | Solvent | Yield (isolated)[a] | Selectivity (AB:BB)[b] |
|---|---|---|---|
|  | HFIP + 18% MeOH HCOOH + 9% MeOH | 61% 45% | >100:1 |
|  |  | 7% |  |
|  | HFIP + 18% MeOH HCOOH + 9% MeOH | 63% 34% | >100:1 >100:1 |

Electrolysis parameters:
n(phenol1) = 5 mmol,
n(phenol2) = 15 mmol,
conductive salt: MTES,
c(MTES) = 0.09M,
V(solvent) = 33 ml,
anode: BDD/Si,
cathode: Ni mesh,
j = 2.8 mA/cm$^2$, T = 50° C.,
Q = 2 F * n(phenol1).
The electrolysis is effected under galvanostatic conditions.
[a] isolated yield based on n(phenol1);
[b] determined via GC.
AB: cross-coupling product,
BB: homo-coupling product.

Table 1 shows that various phenols can be cross-coupled directly with various naphthols by the method described above.

Influence of the Oxidation Potential Differences on Yields and Selectivities

Cyclic voltammetry measurements on substrates used show that differences in individual oxidation potential differences (called $\Delta E_{Ox}$ hereinafter) correlate with selectivities and yields of the electrochemical cross-coupling of phenols.

TABLE 2

| Coupling partner | HFIP pure | 18% MeOH | HFIP pure | 18% MeOH |
|---|---|---|---|---|
| $\Delta E_{ox}$ with 2-naphthol | (4-methyl-2-methoxyphenol) | | (5-methoxy-2-tert-butylphenol) | |
| | GC: 20% + 5% NP | GC: 21% | GC: 25% + 4% NP | GC: 25% |
| | $\Delta = -0.02$ | $\Delta = 0.05$ | $\Delta = 0.0\,5$ V | $\Delta = 0.13$ V |
| Coupling partner | HFIP pure | 18% MeOH | HFIP pure | 18% MeOH |
| $\Delta E_{ox}$ with 2-naphthol | (3-tert-butylphenol) | | (4-isopropyl-2-methylphenol) | |
| | GC: 0% | GC: 0% | GC: 0% | GC: 0% |
| | $\Delta = -0.27$ V | $\Delta = -0.20$ V | $\Delta = -0.27$ V | $\Delta = -0.17$ V |

Working electrode: glassy carbon, counterelectrode: glassy carbon, reference electrode: Ag/AgCl in sat. LiCl/EtOH, v=10 mV/s, oxidation criterion: j=0.10 mA/cm², c(phenol)=0.152 M, conductive salt: MTES, c(MTES)=0.09M. Solvent: HFIP. $\Delta E_{Ox}$=ox.pot.$_{coupling\ partner}$−ox.pot.$_{table\ entry}$. BP: by-products; gas chromatography integration of product ratios.

Addition of MeOH (Entry 1) achieves a reversal in the selectivity for the phenol oxidation. This enables suppression of the naphthol homo-coupling. Increasing $\Delta E_{Ox}$ (Entry 2, HFIP/MeOH system) enables selective formation of the cross-coupling product.

As a result of the addition of methanol, the two oxidation potentials diverge to a sufficient degree (see FIG. 3) that the very selective cross-coupling can successfully be conducted electrochemically.

The invention claimed is:

1. A compound represented by the formula (I) or (III):

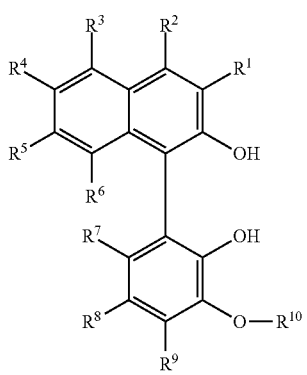

(I)

(III)

wherein
$R^1, R^2, R^3, R^4, R^5, R^6, R^7, R^8, R^9, R^{21}, R^{22}, R^{23}, R^{24}, R^{25}, R^{26}, R^{27}, R^{28}$, and $R^{30}$ are —H, -alkyl, —O-alkyl, —O-aryl, —S-alkyl, or —S-aryl, and $R^{10}$ and $R^{29}$ are -alkyl.

2. The compound according to claim 1, wherein $R^1, R^2, R^3, R^4, R^5, R^6, R^{21}, R^{22}, R^{23}, R^{24}, R^{25}, R^{26}, R^{27}, R^{28}$, and $R^{30}$ are —H or -alkyl.

3. The compound according to claim 1, wherein $R^8$ and $R^{27}$ are -alkyl.

4. The compound according to claim 1, wherein $R^1, R^2, R^3, R^4, R^5, R^6, R^7, R^8, R^9, R^{21}, R^{22}, R^{23}, R^{24}, R^{25}$, and $R^{26}$ are —H.

5. The compound according to claim 1, wherein $R^7, R^9, R^{28}$, and $R^{30}$ are —H.

6. A compound represented by formula (II):

(II)

wherein
$R^{11}, R^{12}, R^{13}, R^{14}, R^{15}, R^{16}, R^{17}$, and $R^{19}$ are —H, -alkyl, —O-alkyl, —O-aryl, —S-alkyl, or —S-aryl, and $R^{18}$ and $R^{20}$ are -alkyl.

7. The compound according to claim 6, wherein $R^{11}, R^{12}, R^{13}, R^{14}, R^{15}, R^{16}, R^{17}$, and $R^{19}$ are —H.

* * * * *